(12) United States Patent
Weiss

(10) Patent No.: US 6,916,000 B2
(45) Date of Patent: Jul. 12, 2005

(54) APPARATUS AND METHOD FOR CANNULATING RETINAL BLOOD VESSELS

(76) Inventor: Jeffrey N. Weiss, 7600 Ventura La., Parkland, FL (US) 33067

( * ) Notice: Subject to any disclaimer, the term of this patent is extended or adjusted under 35 U.S.C. 154(b) by 275 days.

(21) Appl. No.: 09/949,071

(22) Filed: Sep. 7, 2001

(65) Prior Publication Data

US 2003/0057347 A1 Mar. 27, 2003

Related U.S. Application Data

(63) Continuation-in-part of application No. 09/109,454, filed on Jul. 2, 1998.

(51) Int. Cl.$^7$ ............................................. F16M 13/00
(52) U.S. Cl. .................. 248/558; 248/68.1; 248/125.1; 248/230.4; 248/230.6; 606/130
(58) Field of Search ........................... 248/230.4, 230.6, 248/229.15, 229.13, 229.23, 229.25, 125.1, 558, 125.7, 68.1, 62, 160; 604/80; 128/DIG. 26; 606/130; 600/102, 228, 229, 245

(56) References Cited

U.S. PATENT DOCUMENTS

| | | | | | |
|---|---|---|---|---|---|
| 1,230,873 | A | * | 6/1917 | Crossley | 600/228 |
| 2,554,544 | A | * | 5/1951 | Warner | 359/809 |
| 2,607,881 | A | * | 8/1952 | Anderson | 362/144 |
| 3,178,144 | A | * | 4/1965 | Kimoto | 248/229.15 |
| 3,955,722 | A | * | 5/1976 | Bard | 223/106 |
| D264,875 | S | * | 6/1982 | Crocker | D24/183 |
| 4,573,452 | A | * | 3/1986 | Greenberg | 600/102 |
| 4,605,990 | A | * | 8/1986 | Wilder et al. | 362/581 |
| 4,617,916 | A | * | 10/1986 | LeVahn et al. | 600/228 |
| 5,004,457 | A | * | 4/1991 | Wyatt et al. | 604/158 |
| 5,336,179 | A | * | 8/1994 | Ryan | 604/80 |
| 5,814,030 | A | * | 9/1998 | Hedges et al. | 604/294 |
| 5,871,487 | A | * | 2/1999 | Warner et al. | 606/130 |
| 5,941,877 | A | * | 8/1999 | Viegas et al. | 606/55 |
| 6,110,182 | A | * | 8/2000 | Mowlai-Ashtiani | 606/130 |
| 6,210,325 | B1 | * | 4/2001 | Bartie et al. | 600/229 |
| 6,306,146 | B1 | * | 10/2001 | Dinkler | 606/130 |

OTHER PUBLICATIONS

Electrode manipulators models 1460, 1460–61 as shown in web address "www.kopfinstruments.com/Stereotaxic1460_61.html".*

* cited by examiner

Primary Examiner—Korie Chan
(74) Attorney, Agent, or Firm—Daniel S. Polley, P.A.

(57) ABSTRACT

An apparatus and method for safely cannulating a retinal blood vessel is described. The apparatus consists of a micropipette/microcannula, micromanipulator and positioner mounted to a base, which is attached to a wrist rest commonly used in eye surgery. The micropipette/microcannula is connected to tubing such that a medication may be injected through the micropipette/microcannula into the blood vessel or conversely, a small quantity of material may be removed from a blood vessel. Alternatively, a catheter, wire or stent may be placed through the micropipette/microcannula to treat or diagnose an area remote from the insertion site. The ability to cannulate a retinal blood vessel should be efficacious in the treatment of vein and artery occlusion, ocular tumors and other retinal, vascular and optic nerve disorders that would benefit from diagnosis and/or treatment.

18 Claims, 6 Drawing Sheets

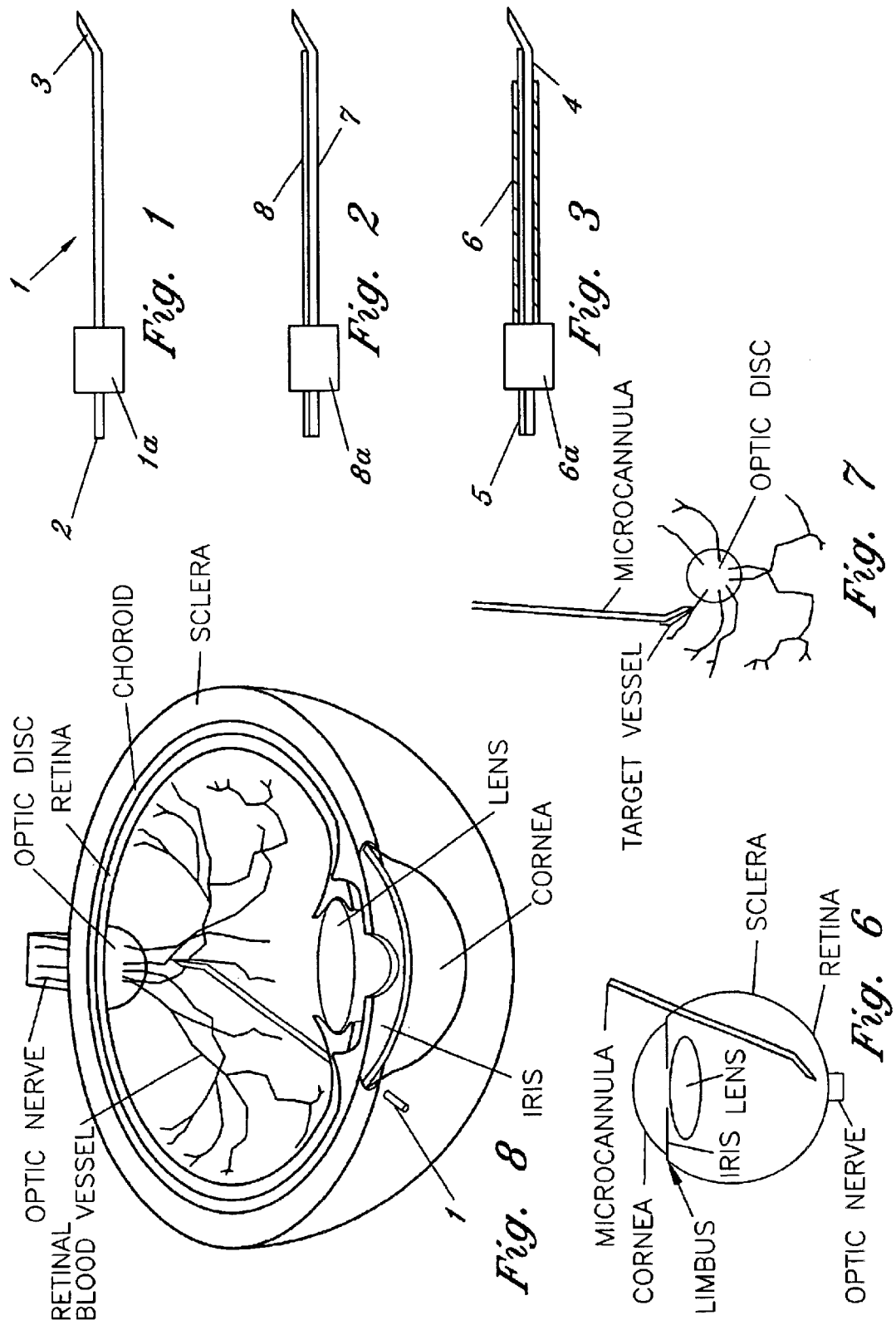

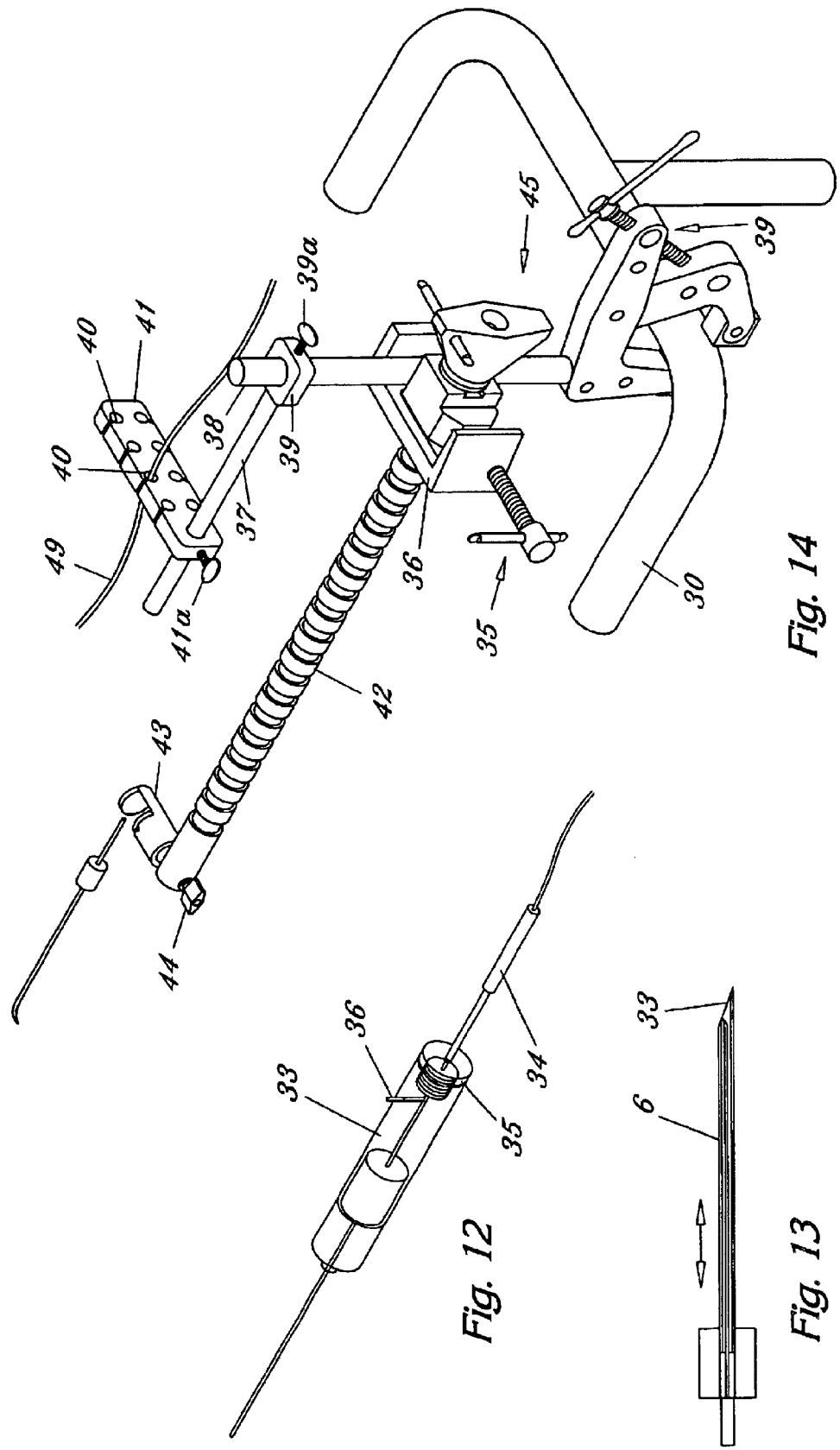

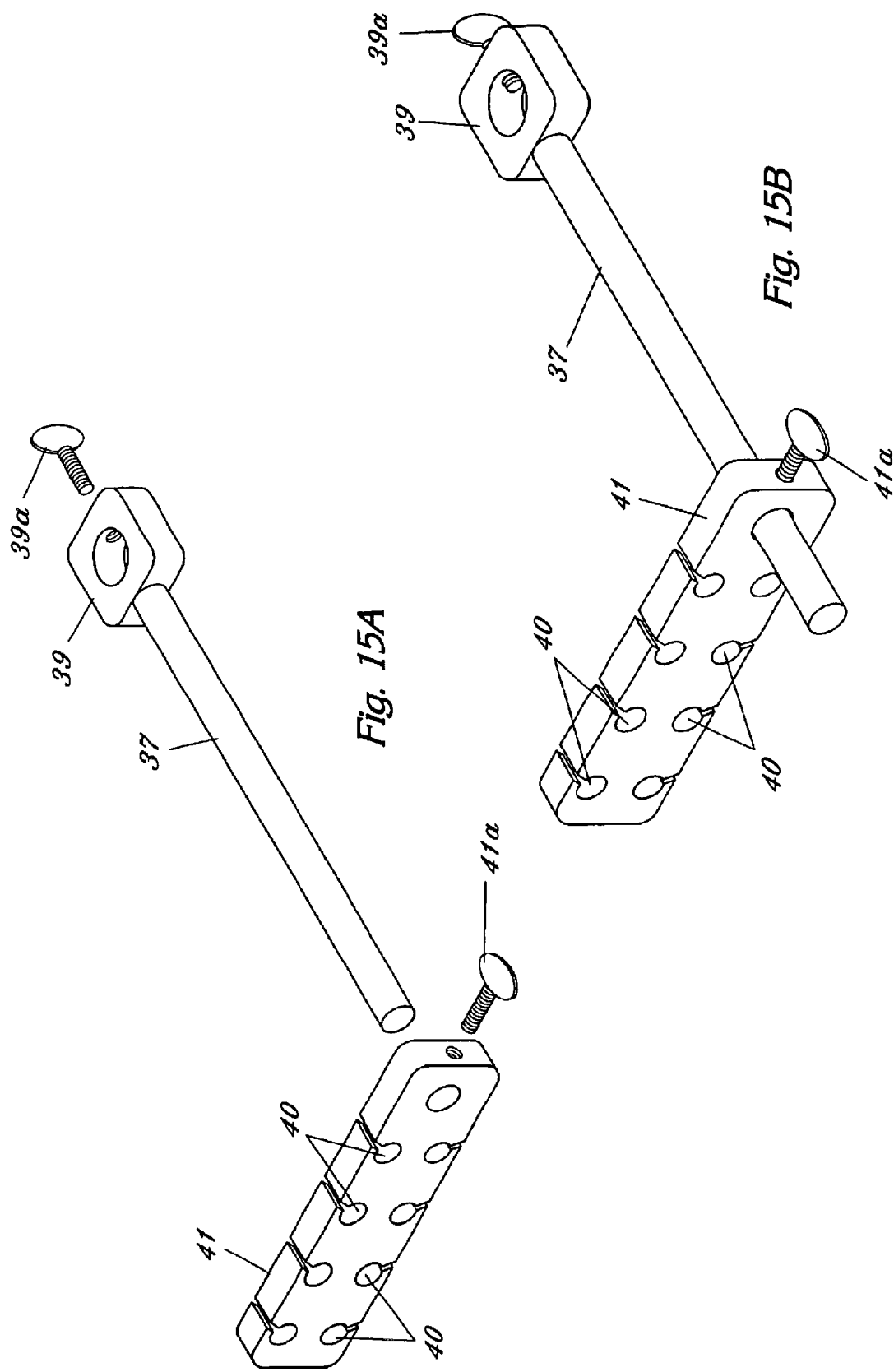

APPARATUS AND METHOD FOR CANNULATING RETINAL BLOOD VESSELS

CROSS-REFERENCE TO RELATED APPLICATIONS

This application is a continuation-in-part of U.S. application Ser. No. 09/109,454, filed Jul. 2, 1998. This invention was disclosed in the Disclosure Documents Program of the U.S. Patent and Trademark Office on May 4, 1998, Disclosure Document No. 435938.

BACKGROUND OF THE INVENTION

1. Field of the Invention

This invention relates to medical diagnostic and therapeutic methods and, in particular, to a method for cannulating a retinal blood vessel such that a medication may be injected or a quantity of fluid removed from the blood vessel. Alternatively, a catheter, wire or stent may be placed through the cannula to treat or diagnose an area remote from the insertion site.

2. Description of Related Art

The cannulation of a retinal blood vessel is difficult as the lumen of the blood vessels is less than 200 microns in size. The present day ocular instruments are too large to cannulate the vessel and the dexterity required to maintain the cannula within the blood vessel for several minutes is not commonly available. The piercing of a blood vessel elsewhere in the body to inject medications, perform surgical procedures or remove blood for analysis and treatment is commonly performed. It is therefore, to the effective resolution of the aforementioned problems and shortcomings that the present invention is directed.

Accordingly, it is an object of this invention to provide a microcannula or micropipette whose lumen is small enough to be safely placed within the lumen of a retinal blood vessel and by its configuration is parallel to the lumen when placed through a standard sclerotomy site, as commonly used in vitreoretinal surgery. The terms microcannula and micropipette are used interchangeably throughout the application. To the extent that such terms differ in any way in meaning, if any, then the broadest definition of the two terms is considered to be the definition for both terms for purposes of the instant invention disclosure.

It is another object of this invention to provide, by its configuration and method of attachment, a stable support such that the micropipette may be securely held within the blood vessel so that subsequent maneuvers may be safely accomplished.

It is still another object of this invention to provide a micromanipulator such that the micropipette may be remotely advanced to perforate the retinal blood vessel.

It is yet another object of this invention to provide a portable device that may be easily attached to a standard operating surgical wrist rest and is stable in its "X", "Y" and "Z" planes.

It is a further object of this invention to provide a device that, by its configuration and method of attachment, does not inhibit the surgeon's view when using an operating microscope or otherwise interfere with the use of the operating microscope.

It is yet another object of this invention to provide a safe method such that the surgical procedure may be performed.

BRIEF SUMMARY OF THE INVENTION

The foregoing objects are achieved and the foregoing problems are solved in the embodiments of the invention in which a retinal blood vessel is cannulated using a micropipette (microcannula) attached to a micromanipulator which is connected to a positioner or stabilization system attached to a standard surgical wrist rest.

More particularly, a sclerotomy can be made at the standard distance from the limbus and an illuminated infusion cannula can be placed through the sclera at this point. A pars plana vitrectomy may or may not be necessary with further experience. Another sclerotomy can be made at the standard distance from the limbus such that the micropipette/microcannula is substantially parallel to the retinal blood vessel chosen to be cannulated. The micropipette is then placed through the sclerotomy overlying the selected retinal blood vessel. The intraocular pressure can be lowered to approximately 5 mm of Mercury to allow dilation of the vessel. Once the blood vessel is perforated, it may be advantageous to raise the intraocular pressure to minimize bleeding. The retinal blood vessel may be cannulated manually or the micromanipulator used to advance the micropipette into the retinal blood vessel.

The micropipette tip is preferably at an approximately 135-degree angle to the shaft such that it is parallel to the lumen of the blood vessel in the posterior retina when placed through a standard sclerotomy site. The tip of the micropipette is preferably 100 microns in diameter or smaller so it may safely enter the lumen of the retinal blood vessel. The opposite end of the micropipette can be connected to and in fluid communication with a standard surgical tubing and/or syringe such that fluid may be withdrawn or injected into the retinal vessel. Alternatively, a catheter or wire may be advanced through the microcannula for diagnosing, testing or treatment of an area located at a distance from the insertion site.

In certain situations medication such as Tissue Plasminogen Activator ("t-PA") made by Genetech, Inc. and sold under the trademark ACTIVASE can be injected into the retinal vessel. Alternatively, a dye can be injected into the retinal vessel for diagnosing purposes.

The micromanipulator is preferably attached to a positioner or stabilization system that is freely mobile and stable in the "X", "Y" and "Z" directions. In the preferred embodiment, the positioner or stabilization system is securely attached to a standard ophthalmic surgery wrist rest by conventional means. The positioner or stabilization system is easy to attach to the wrist rest and may be removed when the device is not needed. At the conclusion of the maneuver, the intraocular pressure may be raised in order to minimize retinal hemorrhaging and the micropipette removed from the blood vessel. The operation is then concluded in standard fashion.

If the illumination is incorporated within the infusion line and infusion cannula then the illumination/infusion line may be placed into a illumination positioner that can be mounted on the stabilization post attached to the surgical wrist-rest. The illumination positioner may be adjustable in the x, y and z planes such that the angle of the fiber optic illumination relative to the eye may be set. This is beneficial in directing the light to the area of the retina that the surgeon is working on.

In another embodiment of the microcannula, a sheath protects the shaft of the microcannula and/or a cover protects the tip of the microcannula during insertion into the eye. Once the microcannula is within the eye the cover is retracted thus exposing the tip. The cover may be slid over the microcannula tip prior to removing the device from the eye in order to minimize tip breakage. A barbed fitting may be attached to the end of the microcannula to aid in attaching the tube that is attached to the syringe.

In an alternate embodiment of the microcannula, the protective tube, needle or larger cannula protects the shaft and the tip of the microcannula and is retracted into the handle to expose the tip. The handle will also protect an otherwise exposed/unprotected portion of the shaft of the microcannula when the protective member is in an extended/outward position over the beveled tip.

If the illumination is incorporated with the microcannula then the illumination component of the infusion cannula may not be necessary. It is also apparent that if an infusion line is required, it may also be incorporated into the microcannula device which may obviate the need for a separate infusion line and/or separate sclerotomy site.

The microcannula may be used to cannulate the retinal vessel manually or alternatively be placed within a holder that aids the surgeon in steadying the device. Another option is to place the microcannula within a micromanipulator such that the microcannula may be manually advanced or automatically advanced into the retinal vessel.

If the retinal vessel chosen for cannulation is in the posterior retina then the microcannula tip is preferably at an approximately 135 degree angle to the shaft such that the tip will be parallel to the lumen of the blood vessel when it is placed through a standard pars plana sclerotomy site. It is apparent that if the blood vessel chosen to be cannulated is in the equatorial or in the peripheral retina than the angle to the shaft would be different so that the microcannula tip will be parallel to the vessel when it is placed through a pars plana sclerotomy site. The location of the sclerotomy site in the eye and its relation to the location of the blood vessel chosen for cannulation affects the tip angle in relation to the shaft. If the microcannula is used to place or remove fluid or material from on top of or underneath the retina than other tip angles are possible.

Fluid may be withdrawn or injected into the retinal vessel or alternatively a catheter, wire, laser fiber, stent, etc. may be advanced through the microcannula for diagnosing, testing or treating an area at or at a distance from the cannulation site. Many other uses of this technology will be apparent to those skilled in the art.

Thus, the present invention provides a device that may safely advance the micropipette into the retinal blood vessel while securely holding it in a stable fashion and allowing rotation in the "X", "Y" and "Z" planes for ease of maneuverability. The apparatus can be easily attached and removed from the operating field, and, is thus portable. The apparatus can be attached by conventional means to the a wrist rest, the operating table, the operating microscope or any other convenient and stable location in the operating room. Additionally, the apparatus is constructed so not to encumber the surgeon's view through the operating microscope, or otherwise interfere with the use of the operating microscope.

In accordance with these and other objects, which will become apparent hereinafter, the instant invention will now be described with particular reference to the accompanying drawings.

BRIEF DESCRIPTION OF THE SEVERAL VIEWS OF THE DRAWINGS

The invention may be better understood by reference to the drawings in which:

FIG. 1 is a front view of a first embodiment for the micropipette (microcannula) of the present invention;

FIG. 2 is a front view of a second embodiment of the micropipette in which an illumination member such as a fiber optic light source is attached to the side of the micropipette to provide illumination during the operation;

FIG. 3 is a front view of a third embodiment of the micropipette wherein the micropipette and fiber optic are enclosed within a protective sheath or tube to minimize breakage when placed into the eye, the protective sheath or tube can also be used for a microcannula without a fiber optic;

FIG. 6 illustrates a view of the micropipette when placed through the sclerotomy site into the eye;

FIG. 7 illustrates the tip of the micropipette overlying and parallel to the retinal blood vessel to be cannulated;

FIG. 8 is a perspective view of the micropipette when placed through the sclerotomy site into the eye;

FIG. 12 illustrates a front view of the seventh embodiment of the microcannula in which the device is encased in a case. The protective sheath may be retracted thus exposing the microcannula tip. An illumination member, such as a fiber optic or other light source may be attached to the microcannula assembly such that the tip of the microcannula or the area surrounding the tip of the microcannula may be illuminated;

FIG. 13 illustrates a front view of the eighth embodiment of the microcannula where the protective sheath may also be substantially sharp;

FIG. 14 is a perspective view of the preferred embodiment for the microcannula, clamp with stabilization post, stabilization arm and illumination positioner attached to a conventional surgeons wrist-rest; and FIG. 15 illustrates the illumination positioning arm that attaches to the stabilization post and an accessory arm that contains a series of openings in which to place a fiber optic thus directing the angle of the illumination within the eye.

DETAILED DESCRIPTION OF THE INVENTION

Figure 4:
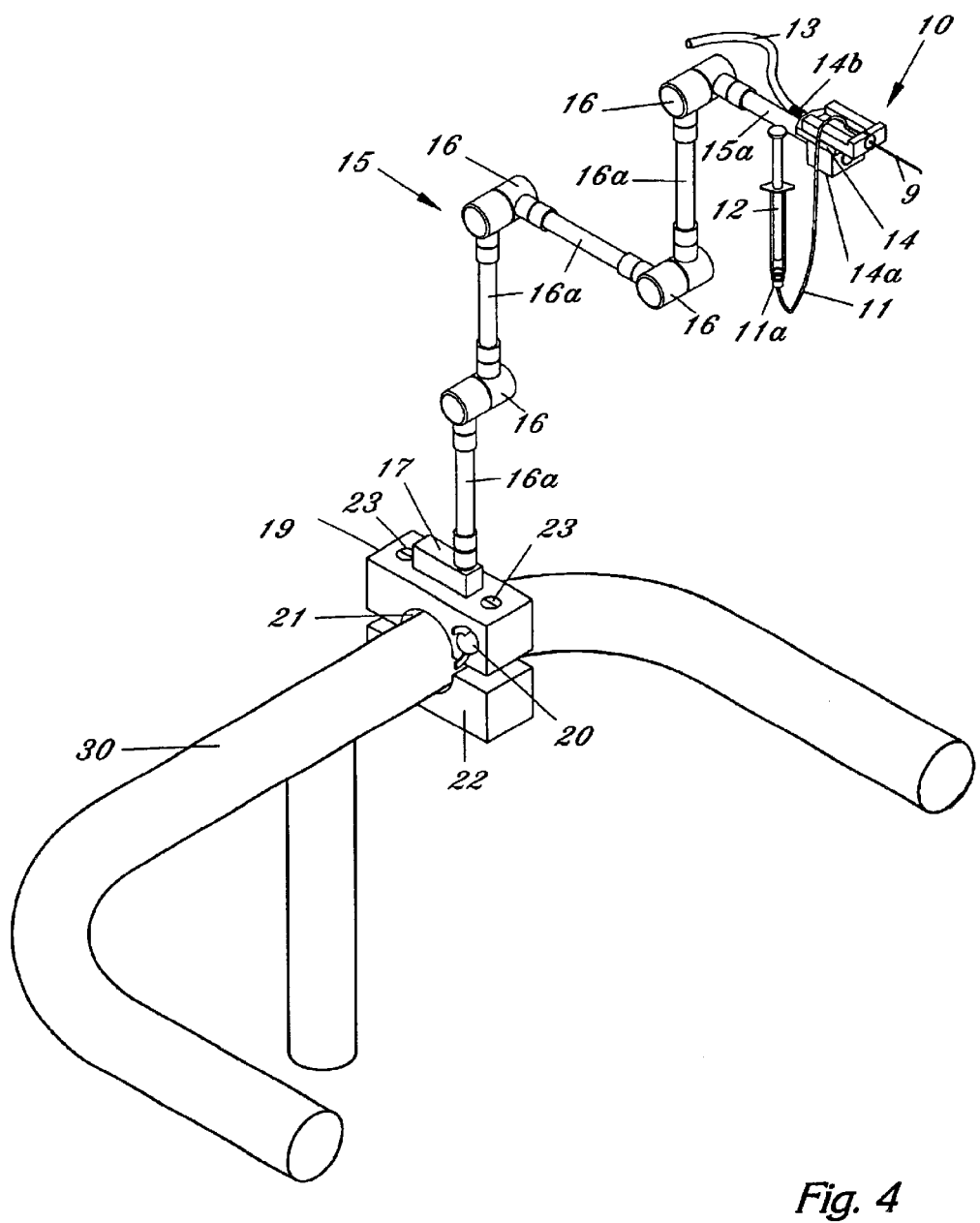
FIG. 4 is a perspective view of the preferred embodiment for the micropipette, micromanipulator, positioner and base of the present invention attached to a conventional wrist rest.

FIG. 1 illustrates a first embodiment for the micropipette/microcannula (1) showing the opening (2) that is preferably connected to a surgical tubing and the tip (3) of the micropipette oriented at an approximately 135 degree angle, although other ranges are possible. Tip (3) is angled so that it may safely cannulate the retinal vessel when micropipette (1) is placed through a standard retinal surgical sclerotomy site. While glass is suggested for the material because of its ease of fashioning, strength, transparency, etc., other materials may be used. It is essential, however, that the materials maintain substantial strength when fashioned to perform retinal vessel cannulation. A handle (1a) is shown attached to the body member of micropipette (1). Handle (1a) fits securely within a micropipette holder (10) by inserting the end of micropipette (1) associated with handle (1a) and handle (1a) into the front opening of holder (10). Once inserted micropipette (1) is held in place by a setscrew associated with the holder (10).

As seen in FIG. 2, an alternative embodiment of the micropipette/microcannula is illustrated. In this embodiment, a fiber optic (8) is attached to the micropipette body (7) to provide illumination such that an illuminated infusion cannula is not required. If a vitrectomy is not performed then one sclerotomy for the micropipette and fiber optic is all that is necessary. A handle (8a) is provided and fits securely within the holder (10) and is held in place by a set screw within the holder (10), similar to as described for micropipette (1).

FIG. 3 illustrates a further alternative embodiment for the micropipette (4) where a fiber optic for illumination is included (5) and both items are placed within a tube or needle (6). The purpose of the tube or needle is to protect the enclosed instruments such that they may be safely inserted through the sclerotomy site without breakage. Both the fiber optic and the micropipette ends are at the end or protrude from the end of the tube or needle. The micropipette and fiber optic may be advanced through the end of the tube or needle once it has been placed within the eye. A handle (6a) is illustrated that fits securely within the holder (10) and may be firmly held in place by a set screw or locking mechanism within the holder (10), as previously described above. If a vitrectomy is not performed then one sclerotomy for this device is all that is necessary.

FIG. 4 illustrates the micropipette (9) attached to the holder (10). A screw handle (14b), which controls the position of the holder (10), is attached to a flexible tube (13) so the micromanipulator may remotely advance the micropipette. Screw handle (14b) is associated with a micromanipulator (14). Preferably, screw handle (14b) is connected to micromanipulator (14). Holder (10) is attached to the micromanipulator. In one embodiment, the micromanipulator is a miniature translation stage, using dual dowel pin bearings. One such micromanipulator is made by the Newport Corporation located in Irvine, Calif. The Newport micromanipulator has a stage, which has a range of travel of approximately four (4 mm) millimeters.

Figure 5:
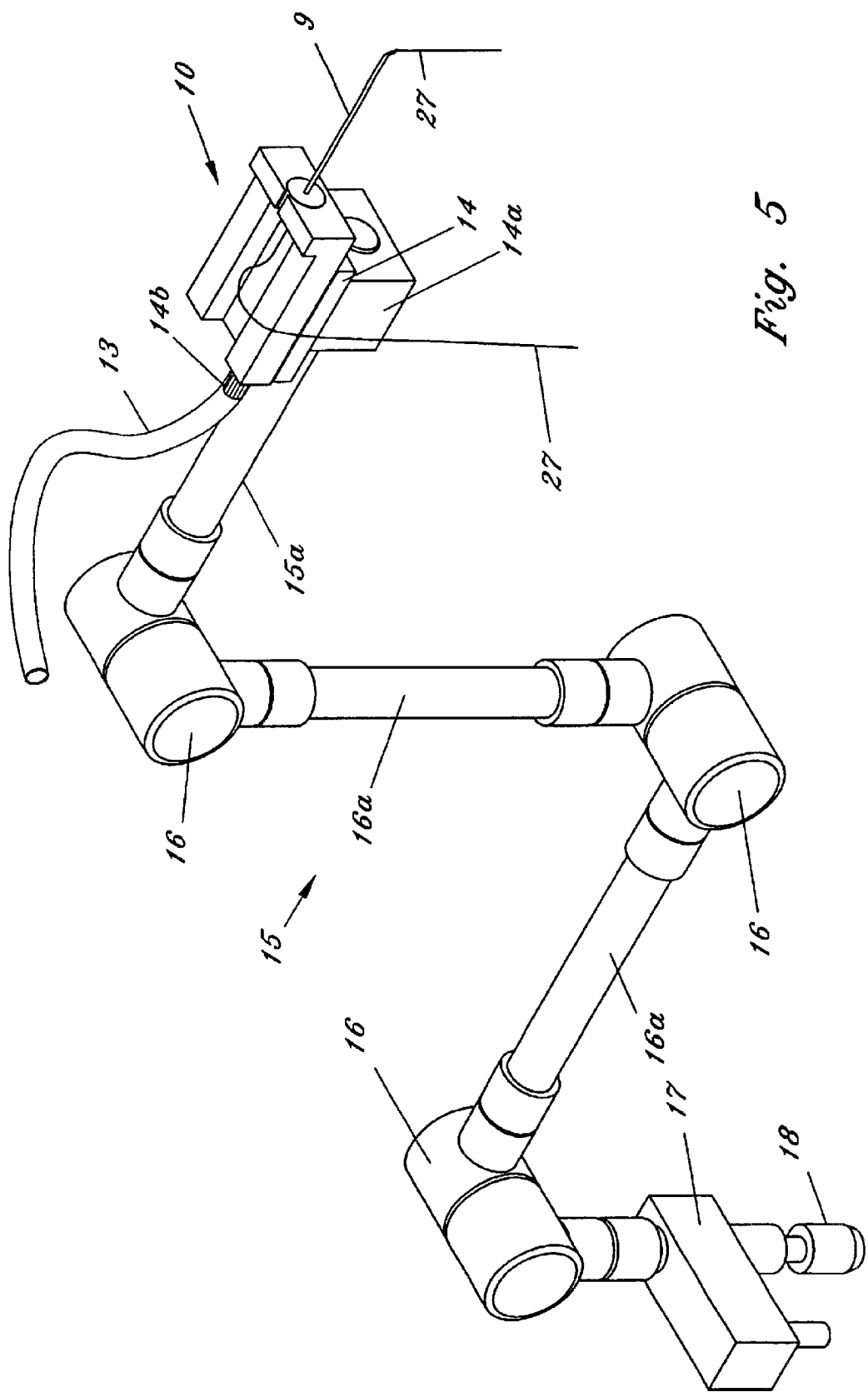
FIG. 5 is another perspective view of the preferred embodiment for the micropipette, micromanipulator, positioner and base of the present invention.

In one embodiment (FIG. 4), the non-tip end of the micropipette is preferably attached to standard surgical tubing (11). The tubing (11) is attached to a connector (11a), which is connected to a syringe (12) that is used to inject medication or withdraw fluid from the retinal blood vessel. In certain situations medication such as t-PA can be injected into the retinal vessel. Alternatively, a dye can be injected into the retinal vessel for diagnosing purposes. Alternatively, a catheter, wire or stent (27) may be advanced through the microcannula for diagnosing, testing or treatment of an area located at a distance from the insertion site (FIG. 5).

It should also be apparent to those skilled in the art that a foot pedal or other switch may control (i.e. electrically, pneumatically, mechanically, etc.) the micromanipulator and injector or withdrawing device so it may be activated by the surgeon. These alternative embodiments are considered within the scope of the invention.

The micromanipulator (14) is attached to a base (14a) which is attached to a positioner (15) that is freely mobile in the "X", "Y" and "Z" planes due to the multiplicity of joints (16), connected by elongated members (15a and 16a). It would be apparent to those skilled in the art that the positioner may also be electrically controlled by servomotors and activated by the surgeon with a foot pedal or other switch. Such alternatives are also considered within the scope of the invention. Positioner (15) is not limited to any specific amount of elongated members.

The positioner can be attached to a base (17). In one embodiment, an attachment post (18) fits into a hole within another base (19). Preferably, set screws or wing nuts (20), are provided, on either side of the base which is used to secure the post to the base. In order to make the base secure, base (19) attaches to another base (22) by two screws (23). Base (19) fits above the standard ophthalmic surgical wrist rest (30) which is oriented perpendicular to bases (19) and (22). The wrist rest fits within the hole (21) that exists between bases (19) and (22). Base portion (22) completes the base and is located underneath the wrist rest. Alternatively, the positioner may be attached directly to the wrist rest or connected to the operating microscope or operating table. Additionally, the bases can be sized to fit other objects in the operating room. Changes in modifications within the spirit and scope of the invention will be apparent to those skilled in the art. Such modifications and changes are intended to be covered by the claims herein.

As seen in FIGS. 6 through 8, a sclerotomy can be made at the standard distance from the limbus and an illuminated infusion cannula can be placed through the sclera at this point. A pars plana vitrectomy may or may not be necessary with further experience. Another or second sclerotomy can be made at the standard distance from the limbus such that the micropipette/microcannula is substantially parallel to the retinal blood vessel chosen to be cannulated. The micropipette is then placed through the sclerotomy overlying the selected retinal blood vessel. The intraocular pressure can be lowered to approximately 5 mm of Mercury to allow dilation of the vessel. Once the blood vessel is perforated, it may be advantageous to raise the intraocular pressure to minimize bleeding. The retinal blood vessel may be cannulated manually or the micromanipulator used to advance the micropipette into the retinal blood vessel.

Figure 9A:
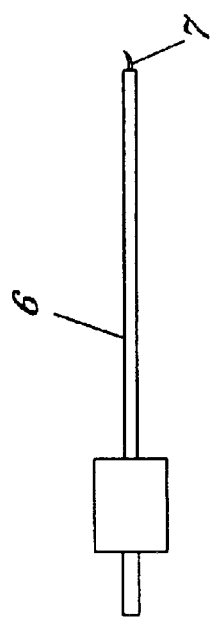
FIG. 9 illustrates a front view of the fourth embodiment of the microcannula in which the shaft of the microcannula is enclosed by a protective sheath.
Figure 9B:
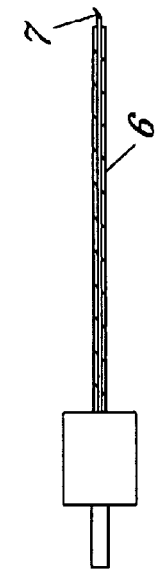

FIGS. 9A and 9B illustrate a front view of the fourth embodiment of the microcannula in which the shaft (7) of the microcannula is enclosed by a protective sheath (6).

Figure 10A:
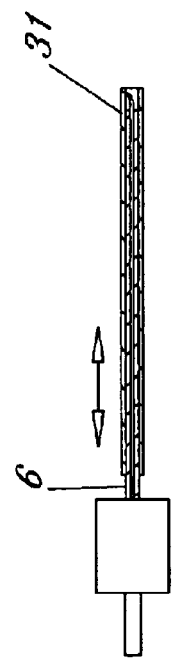
FIG. 10 illustrates a front view of the fifth embodiment of the microcannula in which the shaft of the microcannula is enclosed within a protective sheath with a cover that retracts and exposes the tip of the microcannula.
Figure 10B:
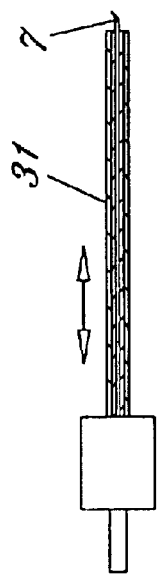

FIGS. 10A and 10B illustrate a fifth embodiment for the microcannula showing the microcannula (7) within a protective sheath (6) that protects the shaft of the microcannula and protective cover (31) that protects the tip of the microcannula (FIG. 10A). The protective sheath and cover may be made of metal, plastic, or other materials that protects the shaft and tip of the microcannula. As seen in FIG. 10B, the cover may be retracted once the microcannula is within the eye and is replaced or extended outwards once the procedure is complete and the microcannula is ready for removal from the eye, such that tip breakage is minimized.

Figure 11A:
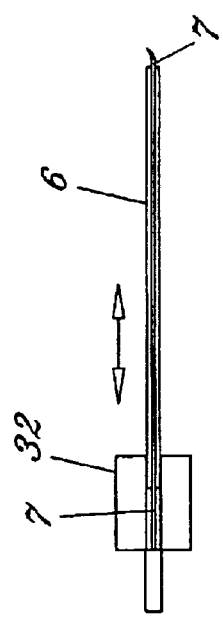
FIG. 11 illustrates a front view of the sixth embodiment of the microcannula in which the protective sheath may be retracted thus exposing the microcannula tip.
Figure 11B:
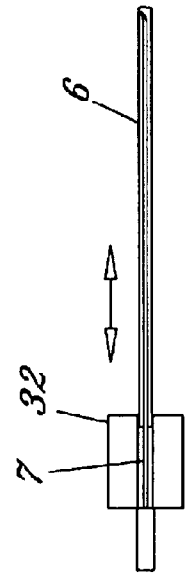

FIGS. 11A and 11B illustrate a front view of the sixth embodiment of the microcannula in which the protective sheath (6) may be retracted into the handle (32) thus exposing the microcannula tip (FIG. 11A). Handle (32) also protects an otherwise exposed/unprotected portion of the shaft (7) of the microcannula when the protective member is in an extended/outward position over the beveled tip (FIG. 11B). The handle attached to the various microcannulas of the invention, including but not limited to handle (32) can be constructed from various materials such as nylon, plastic, delfin, etc.

FIG. 12 illustrates a seventh embodiment for the microcannula, wherein a portion of the shaft of the microcannula is encased in a hard case (33) which may be made from plastic, metal, or another robust material. An illumination member, such as a fiber optic (34) traditionally used in retinal surgery, or another illumination member or light source, may be attached to the case and secured in place by a gasket assembly (35). The type of light source and method of attachment will determine the size and degree of illumination provided. Alternatively, the light member may be attached within or outside the protective cover. The side port (36) is in communication with a device or tubing that is connected to a syringe or other device that will allow the injection or egress of fluid or other material through the microcannula.

FIG. 13 illustrates an alternate embodiment for the microcannula assembly where the tip (33) of the sheath (6) surrounding the microcannula may be sharp enough to perforate the sclera. This embodiment obviates the need for the traditional knife or MVR blade that is generally used by the surgeon to make a hole in the sclera, or sclerotomy, through which the surgeon places instruments into the eye. Once the device is inside the eye, the sheath (6) is retracted exposing the tip of the microcannula and the procedure is performed.

FIG. 14 illustrates a microcannula (i.e. any of the microcannulas disclosed herein) which can be attached to a stabilization arm (42) by a holder (43) and set screw assembly (44) or similar device. The holder (43) includes a clamp mechanism that allows for different sizes of microcannulas to be retained. The stabilization arm (42) is preferably maneuverable in the x-y-z positions and may be connected by another set screw assembly (35) with clamp mechanism (36) or similar device to a stabilization post (38) which can be attached to a clamp (39) that can be attached to a standard surgical wrist-rest (30) or other object. The tension within the stabilization arm is controlled by a tension control assembly (45). The tension along the stabilization arm controls the flexibility of the arm. The stabilization arm may be loosely tightened such that it is sufficiently flexible along its length and allows the microcannula to be easily placed into the eye. Prior to the cannulation of the retinal blood vessel, the tightening of the stabilization arm by the tension control assembly is performed such that the microcannula is steady within the eye, but where small movements are still possible with mild force by the surgeon, if desired. This allows the surgeon to place the microcannula within the blood vessel and allows it to maintain its position within the blood vessel during an infusion of medication, withdrawal of a sample, placement of an instrument, etc. The force required by the surgeon against the stabilization arm dampens any unintended movement by the surgeon such as tremor which may occur during the procedure.

FIGS. 15A and 15B illustrate the illumination positioning arm (37). As seen in FIG. 14, illumination positioning arm (37) attaches to the stabilization post (38) through circular member (39). The arm is held in place by a set screw (39a). One or more, and preferably a series of, openings (40) are placed within an accessory arm (41) that is secured to the illumination positioning arm by a set screw (41a). By setting the angle of the illumination positioning arm in relation to the patient's head, the location of the accessory arm, and the opening in which the fiber optic (49) is placed, the desired location/intensity of illumination within the eye is achieved.

The stabilization arm, stabilization post and illumination positioning arm and accessory arm are preferably made from an easily sterilizable material, such as stainless steel or rubber, though other materials may be used and are considered within the scope of the invention.

In all embodiments, the micropipette/microcannula can be preferably designed to fit a eighteen (18) through twenty (20) gauge sclerotomy site. However, such is not limiting and other gauge sclerotomy sites can be chosen, and the micropipette designed accordingly, and are considered within the scope of the invention.

Though not to be considered limiting, the dimension ranges for the micropipette/microcannula for all embodiments, can preferably consist of the following:

(a) first body portion associated with beveled tip end—length approximately 500–1000 microns;

(b) tip end beveled at approximately twenty (20°)–thirty (30°) degrees;

(c) second body portion associated with handle—length approximately 60–100 millimeters;

(d) beveled tip end—outer diameter approximately 50–100 microns—inner diameter approximately 40–70 microns; and (e) angle between first body portion and second body portion approximately 100°–180°, depending on area in which it is used for.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. An apparatus for positioning a microcannula for use during eye surgery, said apparatus comprising:

means for retaining a microcannula; and means for positioning said means for retaining; and an illumination positioning arm associated with said means for positioning and an accessory arm attached to said illumination positioning arm such that said accessory arm may be attached at different positions along said illumination positioning arm and at different angular positions with respect to said illumination positioning arm, said accessory arm having at least one opening.

2. The apparatus of claim 1, wherein said means for positioning permitting three dimensional movement of said means for retaining prior to using the microcannula to perforate a retinal blood vessel;

wherein said means for retaining is a holder having a microcannula receiving slot and a set screw retaining assembly; wherein a microcannula is disposed within the receiving slot and the set screw retaining assembly is operated to retain the microcannula in its disposed position within the receiving slot.

3. The apparatus of claim 2 wherein said set screw retaining assembly applies pressure directly to said microcannula to retain said microcannula.

4. The apparatus of claim 1 wherein said means for positioning comprises:

a stabilization arm having a first end and a second end, said means for retaining attached approximately at the first end of said stabilization arm, said stabilization arm including a tightening member; and means for securing the stablization arm to an object.

5. The apparatus of claim 4 wherein said means for securing comprises:

a post;

a mounting clamp attached to said post; and means for attaching said post approximately at the second end of said stabilization arm.

6. The apparatus of claim 5 wherein said means for attaching is a set screw retaining assembly disposed at the second end of said stabilization arm.

7. The apparatus of claim 5 wherein said stabilization arm may be attached at different positions along said post and at different angular positions with respect to said post.

8. The apparatus of claim 4 wherein said tightening member is a set screw tightening/loosening ssembly.

9. The apparatus of claim 4 wherein said object is a wrist rest.

10. The apparatus of claim 1 wherein said accessory arm is attached to said illumination position arm by a set screw assembly.

11. The apparatus of claim 1 wherein said accessory arm having a plurality of openings.

12. An apparatus for positioning a microcannula for use in cannulating retinal blood vessels, said apparatus comprising:

a holder having a microcannula receiving slot and a first set screw retaining assembly, wherein a microcannula is disposed within the receiving slot and the first set screw retaining assembly is operated to retain the microcannula in its disposed position within the receiving slot;

a stabilization arm having a first end and a second end, said holder attached approximately at the first end of said stabilization arm, said stabilization arm including a set screw tightening/loosening assembly;

a post attached approximately at the second end of the stabilization arm by a second set screw retaining assembly;

a mounting clamp attached to said post;

an illumination positioning arm attached to said post above or below an attachment point of said stabilization arm to said post and an accessory arm attached to said illumination positioning arm such that said accessory arm may be attached at different positions along said illumination positioning arm and at different angular positions with respect to said illumination positioning arm, said accessory arm having at least one opening.

13. The apparatus of claim 12 wherein said mounting clamp is attached to a wrist rest.

14. The apparatus of claim 12 wherein said accessory arm is attached to said illumination positioning arm by a set screw assembly.

15. The apparatus of claim 12 wherein said accessory arm having a plurality of openings.

16. The apparatus of claim 12 wherein said illumination positioning arm may be attached at different positions along said post and at different angular position with respect to said post.

17. The apparatus of claim 16 wherein said illumination positioning arm is attached to said post by a set screw assembly.

18. The apparatus of claim 12 wherein said stabilization arm may be attached at different positions along said post and at different angular positions with respect to said post.

* * * * *

UNITED STATES PATENT AND TRADEMARK OFFICE
CERTIFICATE OF CORRECTION

PATENT NO. : 6,916,000 B2
DATED : July 12, 2005
INVENTOR(S) : Jeffrey N. Weiss

It is certified that error appears in the above-identified patent and that said Letters Patent is hereby corrected as shown below:

Column 9,
Line 12, delete "ssembly" and insert -- assembly --.
Line 16, delete "position" and insert -- positioning --.

Signed and Sealed this

Eighth Day of November, 2005

JON W. DUDAS
*Director of the United States Patent and Trademark Office*